United States Patent [19]
Sato et al.

[11] Patent Number: 5,665,846
[45] Date of Patent: Sep. 9, 1997

[54] FLUORINATED AMIDE COMPOUNDS AND CURABLE COMPOSITIONS

[75] Inventors: Shinichi Sato; Noriyuki Koike; Takashi Matsuda; Yasushi Yamamoto, all of Usui-gun, Japan

[73] Assignee: Shin-Etsu Chemical Co., Ltd., Tokyo, Japan

[21] Appl. No.: 590,318

[22] Filed: Jan. 23, 1996

[30] Foreign Application Priority Data

Jan. 23, 1995 [JP] Japan .................... 7-027296
Jan. 23, 1995 [JP] Japan .................... 7-027297

[51] Int. Cl.$^6$ .................................................. C08L 77/04
[52] U.S. Cl. .......................... 528/15; 528/31; 528/42; 528/26; 528/28; 556/419
[58] Field of Search .......................... 528/15, 31, 42, 528/26, 28; 556/419

[56] References Cited

U.S. PATENT DOCUMENTS

| | | | |
|---|---|---|---|
| 4,100,136 | 7/1978 | Carter et al. | 528/42 |
| 5,208,312 | 5/1993 | Boutevin et al. | 528/28 |
| 5,300,613 | 4/1994 | Kishita et al. | 528/26 |
| 5,352,752 | 10/1994 | Koike et al. | 528/26 |
| 5,380,811 | 1/1995 | Kishita et al. | 528/15 |
| 5,416,183 | 5/1995 | Sato et al. | 528/15 |

FOREIGN PATENT DOCUMENTS

| | | |
|---|---|---|
| 542471 | 5/1992 | European Pat. Off. |
| 573282 | 6/1993 | European Pat. Off. |

*Primary Examiner*—Ralph H. Dean
*Attorney, Agent, or Firm*—Millen, White, Zelano & Branigan, P.C.

[57] ABSTRACT

Novel fluorinated amide compounds are of formula (1):

$$CH_2=CHSi(R^1)(R^1)\text{-}Ar\text{-}N(R^2)\text{-}C(O)\text{-}[Rf\text{-}C(O)\text{-}Q\text{-}C(O)]_a\text{-}Rf\text{-}C(O)\text{-}N(R^2)\text{-}Ar\text{-}Si(R^1)(R^1)CH=CH_2 \quad (1)$$

wherein $R^1$ is a monovalent hydrocarbon group; $R^2$ is a hydrogen atom or a monovalent hydrocarbon group; Q is a group represented by formula (2) or (3):

$$-N(R^2)-R^3-N(R^2)- \quad (2)$$

$$-N\underset{R^5}{\overset{R^4}{\diagdown\diagup}}N- \quad (3)$$

wherein $R^3$ is a divalent hydrocarbon group which may have at least one intervening atom selected from oxygen, nitrogen and silicon atoms, $R^4$ and $R^5$ are divalent hydrocarbon groups; Rf is a divalent perfluoroalkylene or perfluoropolyether group; and a is an integer inclusive of 0. A curable composition comprising (A) a fluorinated amide compound of formula (1), (B) a fluorinated organohydrogensiloxane containing at least one monovalent perfluorooxyalkyl or perfluoroalkyl or divalent perfluorooxyalkylene or perfluoroalkylene group and at least two hydrosilyl groups, and (C) a platinum group compound cures into elastomers having improved solvent and chemical resistance.

15 Claims, 3 Drawing Sheets

FLUORINATED AMIDE COMPOUNDS AND CURABLE COMPOSITIONS

FIELD OF THE INVENTION

This invention relates to novel fluorinated amide compounds which are useful as stock materials for rubber materials having heat, solvent and chemical resistance and release agents. It also relates to curable compositions which when allowed to stand at room temperature or heated, will readily cure into products having improved solvent, chemical and heat resistance, low-temperature properties, and moisture impermeability.

BACKGROUND OF THE INVENTION

Curable fluorinated elastomer compositions comprising a polymer of fluorinated organic compound and a crosslinking agent have been used in a variety of fields. Such compositions are cured into elastomers which are utilized, for example, as rubber, paint and mold release agents.

Most cured products of conventional fluorinated elastomer compositions, however, are unsatisfactory in solvent resistance, chemical resistance, heat resistance, low-temperature properties and moisture impermeability. For example fluoro-rubber has poor low-temperature properties and cannot be liquefied. Silicone rubber has poor chemical resistance and solvent resistance. Fluorosilicone rubber, which was developed as a rubber material having combined properties of both, is insufficient in chemical resistance and resistance to polar solvents.

Fluorinated elastomers and resins used as paint and mold release agents are desired to exhibit better mold release and water repellent properties.

SUMMARY OF THE INVENTION

An object of the present invention is to provide a novel and improved fluorinated amide compound which will form a cured product having improved solvent resistance, chemical resistance, heat resistance, low-temperature properties, and moisture impermeability.

Another object of the present invention is to provide a curable composition comprising a fluorinated amide compound and a fluorinated organohydrogensiloxane.

We have found that a novel fluorinated amide compound of the following general formula (1) is obtained by reacting a compound having an acid fluoride group at either end of the following general formula (4) with a secondary amine compound of the following general formula (5) or by reacting a compound of formula (4) with a compound of the following general formula (6) and then with a compound of formula (5) and that this fluorinated amide compound of formula (1) can form an elastomer having an increased fluorine content and low surface energy.

In these formulae, $R^1$ is a substituted or unsubstituted monovalent hydrocarbon group, $R^2$ is a hydrogen atom or a substituted or unsubstituted monovalent hydrocarbon group, Q is a group represented by the following general formula (2) or (3):

wherein $R^3$ is a substituted or unsubstituted divalent hydrocarbon group which may have at least one intervening atom selected from oxygen, nitrogen and silicon atoms, $R^4$ and $R^5$ are independently selected from substituted or unsubstituted divalent hydrocarbon groups, Rf is a divalent perfluoroalkylene or perfluoropolyether group, and letter a is an integer inclusive of 0.

We have also found that by blending a fluorinated organosiloxane as a crosslinking agent and a chain extending agent with the fluorinated amide compound of formula (1) and adding a platinum group compound as a catalyst, there is obtained a curable composition which will cure into a product having improved solvent resistance, chemical resistance, heat resistance, low-temperature properties, and moisture impermeability.

Therefore, the present invention in one aspect provides a fluorinated amide compound of formula (1).

In another aspect, the present invention provides a curable composition comprising (A) a fluorinated amide compound of formula (1), (B) a fluorinated organohydrogensiloxane containing at least one monovalent perfluorooxyalkyl, monovalent perfluoroalkyl, divalent perfluorooxyalkylene or divalent perfluoroalkylene group and at least two hydrosilyl groups in a molecule, and (C) a catalytic amount of a platinum group compound. Component (B) is present in an amount to give 0.5 to 5 mol of the hydrosilyl (Si—H) group per mol of the aliphatic unsaturated group in the composition.

BEST MODE FOR CARRYING OUT THE INVENTION

The fluorinated amide compound of the present invention is represented by the general formula (1).

$R^1$ in formula (1) is a substituted or unsubstituted monovalent hydrocarbon group, preferably having 1 to 10 carbon atoms, more preferably 1 to 8 carbon atoms and preferably free of an aliphatic unsaturated bond. $R^2$ is a hydrogen atom or a monovalent hydrocarbon group as represented by $R^1$. Exemplary monovalent hydrocarbon groups represented by $R^1$ and $R^2$ include alkyl groups such as methyl, ethyl, propyl, isopropyl, butyl, isobutyl, tertbutyl, hexyl, octyl, and decyl; cycloalkyl groups such as cyclopehtyl, cyclohexyl, and cycloheptyl; alkenyl groups such as vinyl, allyl, propenyl, isopropenyl, butenyl, isobutenyl, hexenyl, and cyclohexenyl; aryl groups such as phenyl, tolyl, xylyl, and naphthyl; aralkyl groups such as benzyl, phenylethyl, phenylpropyl, and methylbenzyl; and substituted ones of these groups wherein some or all of the hydrogen atoms are replaced by halogen atoms, for example, fluoro-substituted alkyl groups such as chloromethyl, bromoethyl, chloropropyl, 3,3,3-trifluoropropyl, and 6,6,6, 5,5,4,4,3,3-nonafluorohexyl.

Q in formula (1) is a group represented by the following general formula (2) or (3).

$R^2$ in formula (2) is as defined above. $R^3$ is a substituted or unsubstituted divalent hydrocarbon group, preferably having 1 to 20 carbon atoms, more preferably 2 to 10 carbon atoms, for example, alkylene groups such as methylene, ethylene, propylene, methylethylene, butylene, and hexamethylene; cycloalkylene groups such as cyclohexylene; arylene groups such as phenylene, tolylene, xylylene, naphthylene, and biphenylene; substituted ones of these groups wherein some hydrogen atoms are replaced by halogen atoms; and combinations of such substituted or unsubstituted alkylene and/or arylene groups.

The group represented by $R^3$ may have at least one intervening atom within its linkage. The intervening atom is an oxygen, nitrogen or silicon atom. More particularly, the oxygen atom may intervene as —O—. The nitrogen atom may intervene as —NR'— wherein R' is a hydrogen atom, an alkyl group having 1 to 8 carbon atoms, especially 1 to 6 carbon atoms or an aryl group. The silicon atom may intervene as an organosilylene group or as a group containing a linear or cyclic organosiloxane as shown below.

R" is an alkyl group having 1 to 8 carbon atoms or aryl group as exemplified for $R^1$ and $R^2$, R'" is an alkylene group having 1 to 6 carbon atoms or arylene group as exemplified for $R^3$, and n is an integer of 0 to 10, especially 0 to 5.

Examples of the group having an intervening O, N or Si atom represented by $R^3$ are given below. Note that Me is methyl.

$R^4$ and $R^5$ in formula (3) are independently selected from substituted or unsubstituted divalent hydrocarbon groups, preferably having 1 to 10 carbon atoms, more preferably 2 to 6 carbon atoms, for example, alkylene groups such as methylene, ethylene, propylene, methylethylene, butylene, and hexamethylene, cycloalkylene groups such as cyclohexylene and substituted ones of these groups wherein some hydrogen atoms are replaced by halogen atoms.

Examples of the group of formula (2) or (3) represented by Q in formula (1) are given below. Note that in the following chemical formulae, Me is methyl, Ph is phenyl, Rf is as defined below, and X is a hydrogen atom, methyl group or phenyl group.

-continued

In formula (1), Rf is a divalent perfluoroalkylene or perfluoropolyether group. The divalent perfluoroalkylene group is preferably represented by the formula:

$$-C_mF_{2m}-$$

wherein m=1 to 10, preferably 2 to 6. The divalent perfluoropolyether group is preferably represented by the following formulae:

wherein X is F or $CF_3$ group and letters p, q and r are integers in the range: $p \geq 1 q \geq 1$, and $2 \leq p+q \leq 200$, especially $2 \leq p+q \leq 110$ and $0 \leq r \leq 6$, wherein letters r, s and t are integers in the range: $0 \leq r \leq 6$, $s \geq 0$, $t \geq 0$, and $0 \leq s+t \leq 200$, especially $2 \leq s+t \leq 110$, wherein X is F or $CF_3$ group and letters u and v are integers in the range: $1 \leq u \leq 20$ and $1 \leq v \leq 20$, and

$$-CF_2CF_2-(OCF_2CF_2CF_2)_w-OCF_2CF_2-$$

wherein w is an integer in the range: $1 \leq w \leq 100$.

Examples of Rf are given below.

$-C_4F_8-$, $-C_6F_{12}-$,

$\overline{n+m} = 2\text{--}200$, $\overline{n+m} = 2\text{--}200$, $-CF_2CF_2OCF_2(CF_2)_2CF_2OCF_2CF_2-$, $\bar{n} = 5\text{--}50$, $\bar{m} = 1\text{--}10$,

$\bar{n} = 5\text{--}50$, $\bar{m} = 1\text{--}10$, $-CF_2CF_2(OCF_2CF_2CF_2)_nOCF_2CF_2-$  $\bar{n} = 5\text{--}100$ In formula (1), letter a is an integer inclusive of 0. The fluorinated amide compound of formula (1) contains at least one divalent perfluoroalkylene or perfluoropolyether group while a is preferably an integer of 0 to 10, more preferably 1 to 6.

The fluorinated amide compounds of formula (1) according to the invention may be used in various forms covering from low viscosity polymers having a viscosity of several tens of centistokes at 25° C. to solid raw rubber-like polymers. For ease of handling, raw rubber-like polymers are preferred for the intended application as heat vulcanizable rubber and polymers having a viscosity of about 100 to about 100,000 centistokes at 25° C. are preferred for the intended application as liquid rubber. Too low viscosity would be undesirable because cured products would have low elongation as elastomers and imbalance of physical properties.

The fluorinated amide compounds of formula (1) can be obtained by the following method. The fluorinated amide compound of formula (1) wherein a is equal to 0 can be synthesized by reacting a compound having an acid fluoride group at either end of the following general formula (4) with a primary or secondary amine compound of the following general formula (5) in the presence of an acid acceptor such as trimethylamine.

Note that $R^1$, $R^2$ and Rf are as defined previously.

Also the fluorinated amide compound of formula (1) wherein a is an integer of at least 1 can be synthesized by reacting a compound having an acid fluoride group at either end of formula (4) with a diamine compound of the following general formula (6):

$$H-Q-H \qquad (6)$$

wherein Q is as defined previously in the presence of an acid acceptor and further reacting with a primary or secondary amine compound of formula (5).

Although the compound having an acid fluoride group at either end of formula (4) and the primary or secondary amine compound of formula (5) may be used in an desired ratio, it is preferred that the molar ratio of the charge (a) of the formula (4) compound to the charge (b) of the formula (5) compound, (a)/(b), range from 0.1 mol/mol to 1.2 mol/mol, especially from 0.2 mol/mol to 0.5 mol/mol.

Also the compound of formula (4) and the compound of formula (6) are mixed such that the molar charge (a) of the formula (4) compound is not less than the molar charge (c) of the formula (6) compound. The number (represented by a) of recurring units in formula (1) may be controlled to an appropriate value by adjusting the molar ratio (a)/(c). Higher values of (a)/(c) allow for synthesis of polymers having a relatively low molecular weight whereas molar ratios (a)/(c)

approximating to 1 allow for synthesis of polymers having a high molecular weight.

Reaction conditions are not critical. Preferred conditions include a temperature of 20° to 100° C. and a time of about 1 to 8 hours, more preferably a temperature of 20° to 50° C. and a time of about 2 to 4 hours. Among the fluorinated amide compounds of formula (1), those fluorinated amide compounds wherein Q is a group having an intervening silicon atom can be synthesized by selecting an amine compound of formula (5) as a primary or secondary compound having an aliphatic unsaturated group such as vinyl and allyl, subjecting it to the above-mentioned reaction to form a compound having a vinyl group at either end of the following general formula (1'), and further reacting the compound of formula (1') with an organosiloxane compound having two hydrosilyl groups in a molecule of the following general formula (7) in the presence of an addition reaction catalyst.

Note that $R^1$, $R^2$ and Rf are as previously defined.

H—P—H    (7)

Note that P represents a divalent organic group having a siloxane bond as exemplified below.

In this reaction, the compound having a vinyl group at either end of formula (1') and the compound of formula (7) are mixed such that the molar charge (d) of the formula (1') compound is greater than the molar charge (e) of the formula (7) compound. The molar ratio (d)/(e) is at most 2. That is, $1<(d)/(e) \leq 2$. Within this range, higher values of (d)/(e) allow for synthesis of polymers having a relatively low molecular weight whereas molar ratios (d)/(e) approximating to 1 allow for synthesis of polymers having a high molecular weight.

The catalyst used herein is selected from the elements of Group VIII in the Periodic Table and compounds thereof, for example, chloroplatinic acid, alcohol-modified chloroplatinic acid (see U.S. Pat. No. 3,220,972), complexes of chloroplatinic acid with olefins (see U.S. Pat. Nos. 3,159, 601, 3,159,662 and 3,775,452), platinum black and palladium on supports such as alumina, silica and carbon, rhodium-olefin complexes, and chlorotris (triphenylphosphine)rhodium (Wilkinson catalyst). It is used in a catalytic amount. The complexes are preferably used as solution in suitable solvents such as alcohol, ketone, ether and hydrocarbon solvents.

Preferably the reaction is effected at about 50° to 150° C., especially about 80° to 120° C., for about 2 to 4 hours.

The fluorinated amide compounds of the present invention can form elastomers having a high fluorine content and low surface energy, which will find use in a variety of applications as raw materials, for example, base materials for rubber materials having heat, chemical and solvent resistance and base components for mold release agents. For example, elastomers can be obtained by reacting a polymer of a fluorinated amide compound blocked with a vinyl group at either end with a compound having at least three hydrosilyl groups in a molecule in the presence of an addition reaction catalyst. These elastomers exhibit high heat, solvent and chemical resistance because of high fluorine contents and are improved in mold release and water repellency because of low surface energy. Then the elastomers are useful as sealants, molded parts, extruded parts, coating materials and mold release agents.

Also contemplated herein is a curable composition comprising (A) a fluorinated amide compound of formula (1) as a base polymer, (B) a fluorinated organohydrogensiloxane as a crosslinking agent or chain extending agent, and (C) a platinum group compound as a catalyst.

The curable composition of the invention contains components (A), (B) and (C) as essential components. Component (A) is a fluorinated amide compound of formula (1) defined above.

Component (B) is a fluorinated organohydrogensiloxane which serves as a crosslinking agent and chain extender for the fluorinated amide compound (A). The fluorinated organohydrogensiloxane (B) should contain at least one monovalent perfluorooxyalkyl group, monovalent perfluoroalkyl group, divalent perfluorooxyalkylene group or divalent perfluoroalkylene group and at least two, preferably at least three hydrosilyl (Si—H) groups in a molecule. The perfluorooxyalkyl, perfluoroalkyl, perfluorooxyalkylene and perfluoroalkylene groups are preferably those represented by the following general formulae.

monovalent perfluoroalkyl groups:

wherein m is an integer of 1 to 20, preferably 2 to 10.

divalent perfluoroalkylene groups:

wherein m is an integer of 1 to 20, preferably 2 to 10.

monovalent perfluorooxyalkyl groups:

wherein n is an integer of 1 to 5.

divalent perfluorooxyalkylene groups:

wherein m+n is an integer of 2 to 100 on average.

The fluorinated organohydrogensiloxanes may be of cyclic or chain structure or three-dimensional network. They preferably have at least one monovalent organic group having a perfluoroalkyl, perfluoroalkyl ether or perfluoroalkylene group of the following general formula in a molecule as a monovalent substituent attached to a silicon atom.

In the formulae, $R^6$ is a divalent hydrocarbon group, preferably having 1 to 10 carbon atoms, more preferably 2 to 6 carbon atoms, for example, alkylene groups such as methylene, ethylene, propylene, methylethylene, tetramethylene, and hexamethylene, and arylene groups such as phenylene,

$R^7$ is a hydrogen atom or a monovalent hydrocarbon group, preferably having 1 to 8 carbon atoms, more preferably 1 to 6 carbon atoms as defined for $R^2$, and

$Rf^1$ is a monovalent perfluoroalkyl, monovalent perfluorooxyalkyl, divalent perfluorooxyalkylene or divalent perfluoroalkylene group as previously exemplified.

The fluorinated organohydrogensiloxane (B) has a monovalent substituent group attached to a silicon atom other than the monovalent organic group having a monovalent or divalent fluorinated substituent (i.e., perfluoroalkyl, perfluorooxyalkyl, perfluorooxyalkylene or perfluoroalkylene group). Examples of the other substituent group include monovalent hydrocarbon groups free of an aliphatic unsaturated bond, preferably having 1 to 10 carbon atoms, more preferably 1 to 8 carbon atoms as previously defined for $R^2$.

The number of silicon atoms per molecule of the fluorinated organohydrogensiloxane is not critical although it generally has about 2 to 60, preferably about 4 to 30 silicon atoms.

Examples of the fluorinated organohydrogensiloxane are given below. They may be used alone or in admixture of two or more. Note that Me is methyl and Ph is phenyl.

-continued

When the fluorinated organohydrogensiloxane used as component (B) is compatible with the fluorinated amide compound as component (A), the resulting curable composition will yield a uniform cured product.

Component (B) is blended in the composition in such an amount as to provide 0.5 to 5 mol, preferably 1 to 2 mol of the hydrosilyl group (i.e., Si—H group) in component (B) per mol of the aliphatic unsaturated group (e.g., vinyl, allyl and cycloalkenyl groups) in the entire composition, especially component (A). Less than 0.5.mol of the hydrosilyl group on this basis will lead to an insufficient degree of crosslinking. With more than 5 mol of the hydrosilyl group, chain lengthening will become predominant, resulting in short curing or foaming and adversely affecting heat resistance and compression set. Most often, components (A) and (B) are blended such that about 0.1 to 50 parts by weight of component (B) is present per 100 parts by weight of component (A).

The curable composition further contains a platinum group compound as an essential component (C). It is a catalyst for catalyzing addition reaction or hydrosilylation between the fluorinated amide compound and the fluorinated organohydrogensiloxane, that is, serves as a curing promoter. Since the platinum group compounds are generally compounds of noble metals and expensive, relatively easily available platinum compounds are often used.

Illustrative, non-limiting examples of the platinum compound include chloroplatinic acid, complexes of chloroplatinic acid with olefins such as ethylene, complexes of chloroplatinic acid with alcohols or vinylsiloxanes, and platinum on silica, alumina and carbon. Platinum group compounds other than the platinum compounds are also useful. Known examples include compounds of rhodium, ruthenium, iridium, and palladium, for example, such as $RhCl(PPh_3)_3$, $RhCl(CO)(PPh_3)_2$, $RhCl(C_2H_4)_2$, $Ru_3(CO)_{12}$, $IrCl(CO)(PPh_3)_2$, and $Pd(PPh_3)_4$ wherein Ph is phenyl.

On use, these catalysts may be used in solid form if they are solid catalysts. In order to form more uniform cured products, a solution of chloroplatinic acid or its complex in a suitable solvent is preferably used as a miscible mixture with the fluorinated amide compound (A).

The amount of the catalyst used is not critical. A desired curing rate will be achieved with a catalytic amount. From an economical point of view or to produce satisfactory cured products, the catalyst is preferably added in an amount of about 1 to 1,000 ppm, more preferably about 10 to 500 ppm of platinum group element based on the weight of the entire curable composition.

Various additives may be added to the curable composition of the invention in order to enhance their practical usage. Useful additives include polysiloxanes containing a $CH_2=CH(R)SiO$ unit wherein R is hydrogen or a substituted or unsubstituted monovalent hydrocarbon group (see JP-B 10947/1973) and acetylene compounds (see U.S. Pat. No. 3,445,420 and JP-B 3774/1979), which are added for the purpose of controlling the curing rate of the curable composition, and ionic compounds of heavy metals (see U.S. Pat. No. 3,532,649). Where such additives are added, the amount of the fluorinated organohydrogensiloxane blended is determined by taking into account the amount of these additives blended in addition to component (A). More specifically, 0.5 to 5 mol of Si—H group should be present per mol of the aliphatic unsaturated group (e.g., vinyl, allyl and cycloalkenyl groups) in the entire composition as previously mentioned.

Moreover, fillers may be blended in the curable composition of the invention for the purposes of reducing thermal shrinkage upon heating, reducing the coefficient of thermal expansion of elastomers as cured, improving thermal stability, weather resistance, chemical resistance, flame retardancy and mechanical strength, and reducing gas permeability. Exemplary fillers include fumed silica, quartz powder, glass fibers, carbon, metal oxides such as iron oxide, titanium oxide, and cerium oxide, and metal carbonates such as calcium carbonate and magnesium carbonate. If desired, suitable pigments, dyes or anti-oxidants may also be added.

Any desired method may be used in preparing the curable composition according to the invention. The composition can be prepared simply by mixing the above-defined components. The curable composition as mixed can be cured at room temperature depending on the type of functional group in the fluorinated amide compound as the first essential component and the type of catalyst as the third essential component. Preferably the composition is cured by heating at 100° to 150° C. for several minutes to several hours.

On use, the curable composition of the invention may be dissolved in suitable fluorinated solvents such as metaxylene hexafluoride and fluorinates to a desired concentration depending on its application and purpose.

The fluorinated amide compound of the invention can form an elastomer or resin having a high fluorine content and low surface energy which is useful as a base material for rubber materials having heat resistance, solvent resistance and chemical resistance as well as a base material for mold release agents.

The curable composition of the invention will cure into products which exhibit high solvent and chemical resistance because of high fluorine contents, low moisture permeability, and improved mold release and water repellency because of low surface energy. Then the cured products or elastomers are useful as automotive rubber materials required to be oil resistant, tent film materials, sealants, molded parts, extruded parts, coating materials, printing machine roll materials, and electrical moisture-proof coating materials.

EXAMPLE

Examples of the present invention are given below by way of illustration and not by way of limitation. Note that Me is methyl. All parts are by weight.

Example 1

A 1-liter four-necked flask equipped with a stirrer, thermometer, Dimroth condenser, and dropping funnel was charged with 1,000 g of a compound having an acid fluoride group at each end of the following formula (8). With stirring, a mixture of 72.0 g of vinylsilylamine of the following formula (9) and 44.8 g of triethylamine was added. dropwise to the flask at 20° C.

Figure 1:
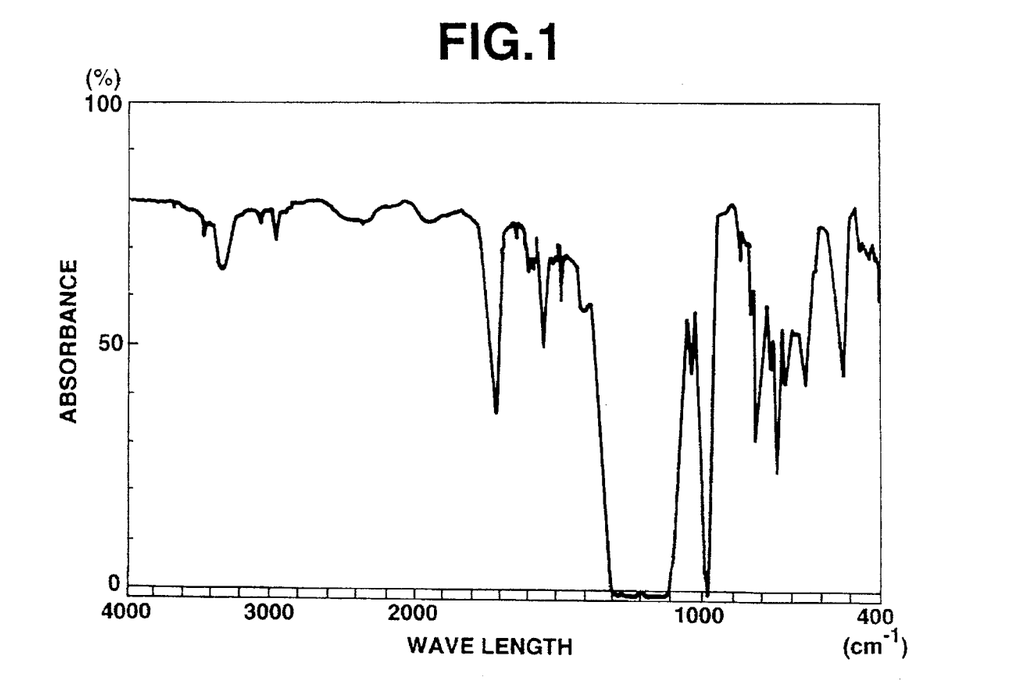
FIG. 1 is an IR spectrum chart of a fluorinated amide compound prepared in Example 1.

After the dropwise addition, reaction was effected at 60° C. for 2 hours. The reaction mixture was subject to filtration under pressure and the filtrate was vacuum stripped at 120° C./3 mmHg, Yielding 989.5 g of a compound as a pale yellow clear liquid. The compound had a viscosity of 9,500 centistokes at 25° C., a specific gravity of 1.829 at 25° C., and a refractive index of 1.3258 at 25° C. The compound was analyzed by IR spectroscopy, with the results shown in FIG. 1. In FIG. 1, the following absorption peaks were observed.

1100–1320 cm$^{-1}$ νC—F

1715 cm$^{-1}$ νC=O

The vinyl content of this compound was quantitatively determined to be 0.035 mol/100 g. From these data, the compound was identified to be a polymer of a fluorinated amide compound represented by the following structural formula (10).

Example 2

A 500-ml four-necked flask equipped with a stirrer, thermometer, Dimroth condenser, and dropping funnel was charged with 500 g of a compound having an acid fluoride group at each end of formula (11). With stirring, a mixture of 12.4 g of vinylsilylaniline of formula (9) and 7.7 g of triethylamine was added dropwise to the flask at 20° C. through the dropping funnel.

(11)

Figure 2:
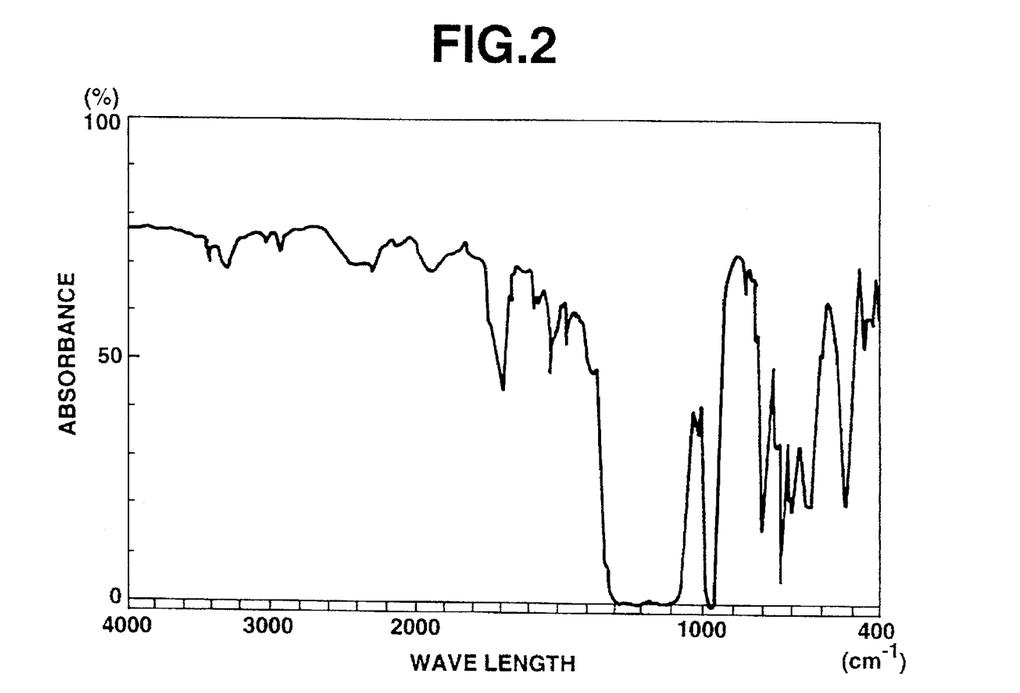
FIG. 2 is an IR spectrum chart of a fluorinated amide compound prepared in Example 2.

After the dropwise addition, reaction was effected at 60° C. for 2 hours. The reaction mixture was subject to filtration under pressure and the filtrate was vacuum stripped at 120° C./3 mmHg, yielding 469.4 g of a compound as a pale yellow clear liquid. The compound had a viscosity of 21,000 centistokes at 25° C., a specific gravity of 1.884 at 25° C., and a refractive index of 1.3136 at 25° C. The compound was analyzed by IR spectroscopy, with the results shown in FIG. 2. In FIG. 2, the following absorption peaks were observed.

1100–1320 cm$^{-1}$ vC—F 1710 cm$^{-1}$ vC=O

The vinyl content of this compound was quantitatively determined to be 0.013 mol/100 g. From these data, the compound was identified to be a polymer of a fluorinated amide compound represented by the following structural formula (12).

Figure 3:
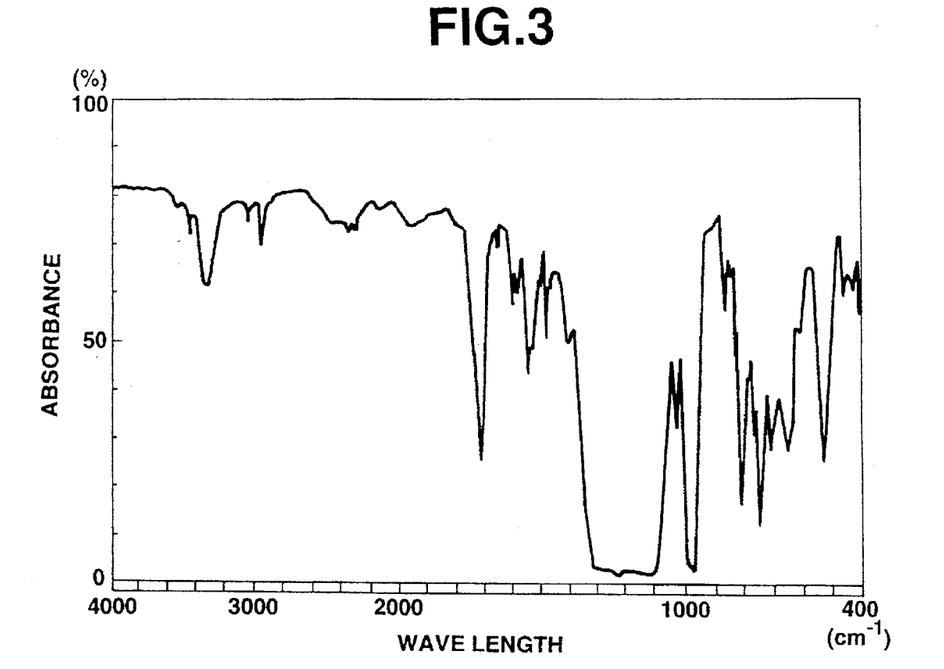
FIG. 3 is an IR spectrum chart of a fluorinated amide compound prepared in Example 3.

The compound had a viscosity of 43,200 centistokes at 25° C. The compound was analyzed by IR spectroscopy, with the results shown in FIG. 3. In FIG. 3, the following absorption peaks were observed.

1100–1320 cm$^{-1}$ vC—F

1705 cm$^{-1}$ vC=O

The vinyl content of this compound was quantitatively determined to be 0.005 mol/100 g. From these data, the compound was identified to be a polymer of a fluorinated amide compound represented by the following structural formula (13).

Example 3

A 200-ml four-necked flask equipped with a stirrer, thermometer, Dimroth condenser, and dropping funnel was charged with 76.9 g of the compound having an acid fluoride group at each end of formula (8). With stirring, a mixture of 1.14 g of 2,5-dimethylpiperazine and 2.9 g of triethylamine was added dropwise to the flask at 20° C. through the dropping funnel. After the dropwise addition, reaction was effected at 60° C. for 2 hours. After 0.36 g of vinylsilylamine of formula (9) was added to the reaction mixture, reaction was effected at 60° C. for 2 hours and post-treatment was done as in Example 1, yielding 72.9 g of a compound as a pale yellow clear liquid.

Example 4

A flask as used in Example 3 was charged with 100.0 g of the compound obtained in Example 1, that is, compound of formula (10) having a vinyl group at each end (viscosity 9,500 centistokes at 25° C.) and 50.0 g of meta-xylene hexafluoride. The flask was heated to 90° C. with stirring and 0.1 g of an isopropyl alcohol solution of 2% chloroplatinic acid was added thereto. Then 4.25 g of a cyclotetrasiloxane of the following formula (14) was added dropwise to the flask through the dropping funnel, allowing reaction to take place.

After the dropwise addition, the reaction solution was aged while the disappearance of the cyclotetrasiloxane was confirmed by gas chromatography. Thereafter, the reaction solution was cooled down to room temperature, and 1.5 g of activated carbon was added to the solution which was agitated for 2 hours. The reaction solution was subject to post-treatment as in Example 1, yielding 99.2 g of a clear liquid compound.

Figure 4:
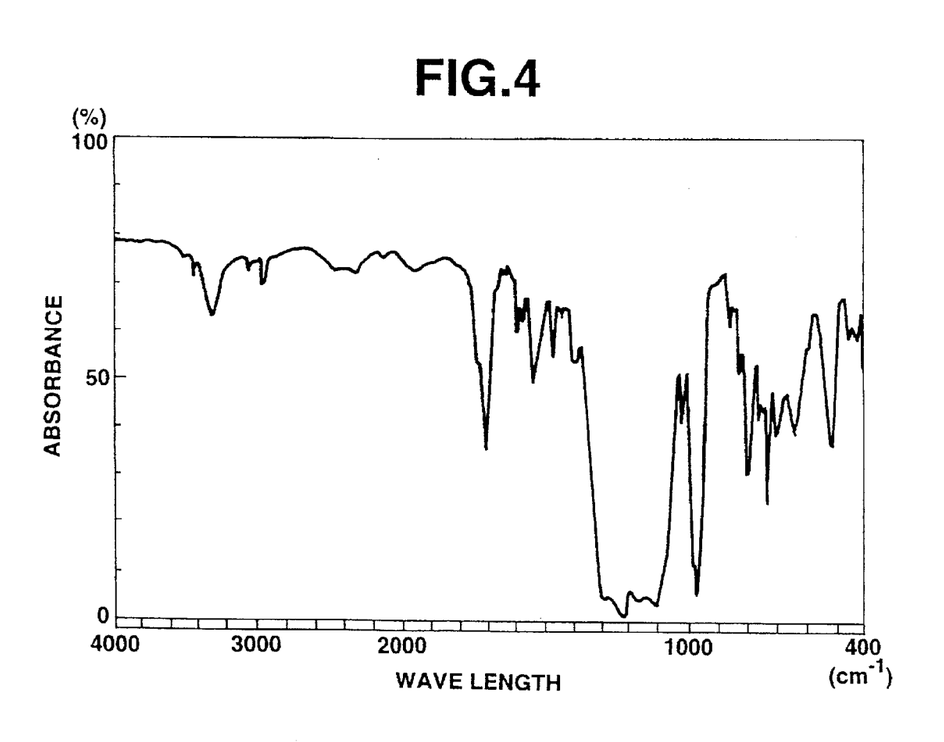
FIG. 4 is an IR spectrum chart of a fluorinated amide compound prepared in Example 4.

The compound had a viscosity of 87,500 centistokes at 25° C. It was analyzed by IR spectroscopy, with the results shown in FIG. 4. In FIG. 4, the following absorption peaks were observed.

1100–1320 cm$^{-1}$ νC—F 1705 cm$^{-1}$ νC=O

The compound was quantitatively determined to find a vinyl content of 0.009 mol/100 g. From these data, the compound was identified to be a polymer of a fluorinated amide compound having the following structural formula (15).

nel was charged with 81.6 g of a compound having an acid fluoride group at each end of the following formula (16). With stirring, a mixture of 2.8 g of vinylsilylaniline of the following formula (17) and 1.0 g of triethylamine was added dropwise to the flask at 20° C. through the dropping funnel.

Figure 5:
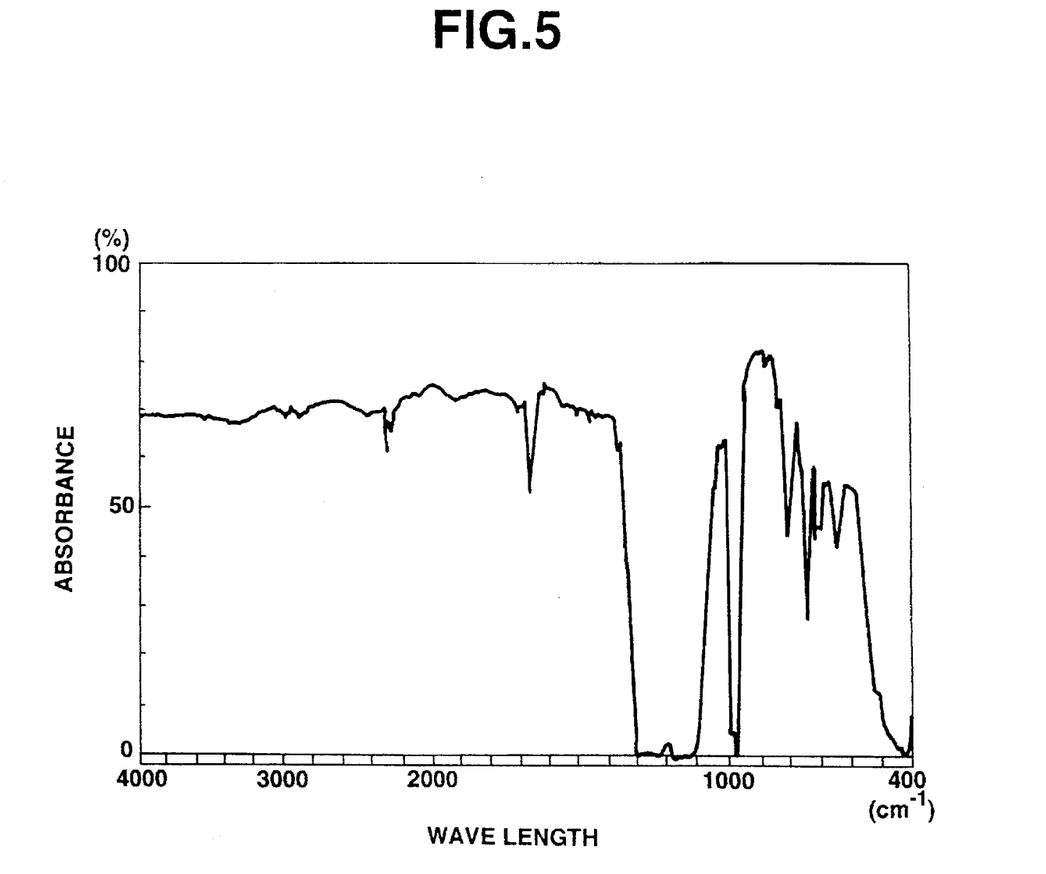
FIG. 5 is an IR spectrum chart of a fluorinated amide compound prepared in Example 5.

After the dropwise addition, reaction was effected at 60° C. for 2 hours. The reaction mixture was subject to filtration under pressure and the filtrate was vacuum stripped at 120° C./3 mmHg, yielding 76.8 g of a compound as a pale yellow clear liquid. The compound had a viscosity of 9,800 centistokes at 25° C., a specific gravity of 1.873 at 25° C., and a refractive index of 1.3126 at 25° C. It was analyzed by IR spectroscopy, with the results shown in FIG. 5. In FIG. 5, the following absorption peaks were observed.

1100–1320 cm$^{-1}$ νC—F 1700 cm$^{-1}$ νC=O

The compound was quantitatively determined to find a vinyl content of 0.013 mol/100 g. From these data, the compound was identified to be a polymer of a fluorinated amide compound having the following structural formula (18).

Rf': as defined in Example 3
Q":

Example 5

A 200-ml four-necked separable flask equipped with a stirrer, thermometer, Dimroth condenser, and dropping fun- (18)

Example 6

To 100 parts of the polymer obtained in Example 1, that is, polymer of formula (10) having a viscosity of 9,500 centistokes at 25° C., an average molecular weight of 5,720 and a vinyl content of 0.035 mol/100 g was added 10 parts of fumed silica having a specific surface area of 200 m²/g and treated with trimethylsiloxy group. They were mixed, heat treated, and milled on a three-roll mill. To the compound were further added 45.0 parts of a fluorinated cyclohydrogensiloxane of the following formula (19) and 0.2 part of a toluene solution of a chloroplatinic acid catalyst modified with $CH_2=CHSiMe_2OSiMe_2CH=CH_2$ (platinum concentration 1.0% by weight), with mixing continued.

(19)

The resulting composition was defoamed under vacuum, placed in a rectangular frame of 2 mm high, deaerated again, and press cured at 120 kg/cm² and 150° C. for 10 minutes. A specimen was cut from the cured sheet and measured for physical properties according to JIS K-6301, with the results shown below.

Hardness (JIS-A) 46

Elongation (%) 240

Tensile strength (kgf/cm²) 59

Note that hardness in JIS A scale was measured using a type A spring hardness tester prescribed in JIS K-6301.

The specimen was also examined for heat resistance, chemical resistance, solvent swell, low-temperature properties, and moisture permeability. The results are shown in Tables 1 to 5.

TABLE 1

| | Heat resistance | | |
|---|---|---|---|
| | Initial | 3 days | 7 days |
| 200° C. | | | |
| Hardness (JIS-A) | 46 | 51 (+5) | 48 (+2) |
| Elongation (%) | 240 | 160 (−33) | 140 (−42) |
| TS (kgf/cm²) | 59 | 44 (−25) | 43 (−27) |
| Heat loss (%) | — | 1.1 | 1.2 |
| 250° C. | | | |
| Hardness (JIS-A) | 46 | 43 (+3) | 42 (−4) |

TABLE 1-continued

| | Heat resistance | | |
|---|---|---|---|
| | Initial | 3 days | 7 days |
| Elongation (%) | 240 | 140 (−42) | 120 (−50) |
| TS (kgf/cm²) | 59 | 31 (−47) | 27 (−54) |
| Heat loss (%) | — | 2.5 | 4.5 |

Note: Figures in parentheses are percents based on the initial for elongation and tensile strength, and increase or decrease of points for hardness.

TABLE 2

| Chemical resistance (change of rubber hardness) | | |
|---|---|---|
| | Hardness | Surface state |
| Initial | 46 | — |
| conc. hydrochloric acid | 55 (+9) | no change |
| conc. sulfuric acid | 48 (+2) | deteriorated |
| 40% potassium hydroxide | 53 (+7) | no change |

Note: Figures in parentheses are increase or decrease of points.
Deterioration conditions: 20° C./3 days

TABLE 3

| | Solvent swell (volume change, %) | | |
|---|---|---|---|
| Solvent | Composition I | Viton GFLT | FE61 |
| Gasoline | +10 | +5 | +42 |
| Methanol | +1 | +16 | +1 |
| Chloroform | +9 | +12 | +23 |
| Acetone | +8 | +148 | +177 |
| Toluene | +1 | +10 | +30 |
| Isopropyl alcohol | +4 | +1 | +1 |
| Acetonitrile | +0 | +46 | +3 |
| Methyl ethyl ketone | +13 | +150 | +194 |
| Ethyl acetate | +14 | +150 | +172 |
| Tetrahydrofuran | +18 | +149 | +204 |
| n-hexane | +4 | +2 | +18 |

TABLE 3-continued

Solvent swell (volume change, %)

| Solvent | Composition I | Viton GFLT | FE61 |
|---|---|---|---|
| Carbon tetrachloride | +8 | +4 | +27 |

Note: Viton GFLT is a fluoroelastomer, Du Pont de Nemours, E.I. & Co. FE61 is a fluorosilicone rubber, Shin-Etsu Chemical Co., Ltd.

TABLE 4

Low-temperature property (German twist test)

| | Composition I | Viton E-60 C. | KE951 |
|---|---|---|---|
| $T_2$ | −10° C. | −6° C. | −41° C. |
| $T_5$ | −36° C. | −11° C. | −43° C. |
| $T_{10}$ | −44° C. | −14° C. | −44° C. |
| $T_{100}$ | −50° C. | −20° C. | −50° C. |

Note: Viton E-60C is a fluoroelastomer, Du Pont de Nemours, E.I. & Co. KE951 is a silicone rubber, Shin-Etsu Chemical Co., Ltd.

TABLE 5

Mositure perrmeability (CUP test)

| Sample | Moisture permeability ($g/m^2 \cdot 24$ hr) |
|---|---|
| Composition I | 4 |
| KE951 | 100 |
| Viton GFLT | 4 |
| FE251 | 50 |

Note:
CUP test under condition B at 40° C. and RH 90%

TABLE 5-continued

Mositure perrmeability (CUP test)

| Sample | Moisture permeability ($g/m^2 \cdot 24$ hr) |
|---|---|

KE951 is a silicone rubber, Shin-Etsu Chemical Co., Ltd. Viton GFLT is a fluoroelastomer, Du Pont de Nemours, E.I. & Co. FE251 is a fluorosilicone rubber, Shin-Etsu Chemical Co., Ltd.

Example 7

A composition was prepared by the same procedure as in Example 6 except that 100 parts of the polymer obtained in Example 2, that is, polymer of formula (12) having a viscosity of 21,000 centistokes at 25° C., an average molecular weight of 16,000 and a vinyl content of 0.013 mol/100 g and 16.3 parts of the fluorinated cyclohydrogensiloxane used in Example 6 were used. A cured sheet was similarly prepared therefrom.

A specimen cut from the cured sheet was similarly measured for physical properties, with the results shown below.

Hardness (JIS-A) 33

Elongation (%) 410

Tensile strength (kgf/cm$^2$) 32

Example 8

A composition was prepared by the same procedure as in Example 6 except that 100 parts of a polymer of the following formula (20) having a viscosity of 128,600 centistokes at 25° C., an average molecular weight of 23,000 and a vinyl content of 0.009 mol/100 g was used instead of the polymer of Example 1 and 11.6 parts of the fluorinated cyclohydrogensiloxane used in Example 6 was used. A cured sheet was similarly prepared therefrom.

A specimen cut from the cured sheet was similarly measured for physical properties, with the results shown below.

Hardness (JIS-A) 31
Elongation (%) 390
Tensile strength (kgf/cm$^2$) 40

Example 9

A composition was prepared by the same procedure as in Example 6 except that 100 parts of a polymer of the following formula (21) having a viscosity of 65,100 centistokes at 25° C., an average molecular weight of 27,640 and a vinyl content of 0.007 mol/100 g was used instead of the polymer of Example 1 and 9.0 parts of the fluorinated cyclohydrogensiloxane used in Example 6 was used. A cured sheet was similarly prepared therefrom.

$$CH_2=CHSi(Me)(Me)-C_6H_4-NH-C(=O)-[Rf^2-C(=O)-Q^2-C(=O)]_4-Rf^2-C(=O)-NH-C_6H_4-Si(Me)(Me)CH=CH_2 \quad (21)$$

$$Rf^2: -(CFOCF_2)_n(CF_2OCF)_m- \quad \overline{n+m}=32$$
$$\qquad\quad |\qquad\qquad |$$
$$\qquad\quad CF_3\qquad\quad CF_3$$

$$Q^2: -N\underset{CH-CH_2}{\overset{CH_2-CH_2}{\diagdown\qquad\diagup}}N-$$
$$\quad\ \ |\qquad\qquad\qquad |$$
$$\ \ CH_3\qquad\qquad\ \ CH_3$$

A specimen cut from the cured sheet was similarly measured for physical properties, with the results shown below.

Hardness (JIS-A) 35
Elongation (%) 450
Tensile strength (kgf/cm$^2$) 49

Example 10

A composition was prepared by the same procedure as in Example 6 except that 100 parts of the polymer obtained in Example 5, that is, polymer of formula (18) having a viscosity of 9,800 centistokes at 25° C., an average molecular weight of 15,380 and a vinyl content of 0.013 mol/100 g was used instead of the polymer of Example 1. To the polymer were added 3.41 parts of a fluorinated cyclohydrogensiloxane of the following formula (22), 0.2 part of the toluene solution used in Example 6, and 0.4 part of 2-ethynylhexanol. A cured sheet was similarly prepared therefrom.

$$C_8F_{17}CH_2CH_2SiO(SiO)_nSiCH_2CH_2C_8F_{17} \quad \overline{n}=8 \quad (22)$$
(with Me, H, Me substituents on the Si atoms as shown)

A specimen cut from the cured sheet was similarly measured for physical properties, with the results shown below.

Hardness (JIS-A) 33
Elongation (%) 260
Tensile strength (kgf/cm$^2$) 26

The specimens were also examined for heat resistance. The results are shown in Table 6.

TABLE 6

| | Heat resistance | | |
|---|---|---|---|
| | Initial | 3 days | 7 days |
| 200° C. | | | |
| Hardness (JIS-A) | 33 | 32 (−1) | 33 (±0) |
| Elongation (%) | 260 | 250 (−4) | 220 (−15) |
| TS (kgf/cm$^2$) | 26 | 24 (−8) | 22 (−15) |
| Heat loss (%) | — | 0.5 | 0.7 |

TABLE 6-continued

| | Heat resistance | | |
|---|---|---|---|
| | Initial | 3 days | 7 days |
| 250° C. | | | |
| Hardness (JIS-A) | 33 | 30 (−3) | 29 (−4) |
| Elongation (%) | 260 | 240 (−8) | 230 (−12) |
| TS (kgf/cm$^2$) | 26 | 23 (−12) | 19 (−27) |
| Heat loss (%) | — | 1.1 | 1.5 |

Note: Figures in parentheses are percents based on the initial for elongation and tensile strength, and increase or decrease of points for hardness.

Japanese Patent Application No. 27297/1995 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A fluorinated amide compound of the following general formula (1):

(1)

wherein $R^1$ is a substituted or unsubstituted monovalent hydrocarbon group, $R^2$ is a hydrogen atom or a substituted or unsubstituted monovalent hydrocarbon group, Q is a group represented by the following general formula (2) or (3):

(2)

(3)

wherein $R^3$ is a substituted or unsubstituted divalent hydrocarbon group which may have at least one intervening atom selected from oxygen, nitrogen and silicon atoms, $R^4$ and $R^5$ are independently selected from substituted or unsubstituted divalent hydrocarbon groups, Rf is a divalent perfluoroalkylene or perfluoropolyether group, and letter a is an integer inclusive of 0.

2. A curable composition comprising (A) a fluorinated amide compound of formula (1) as set forth in claim 1, (B) a fluorinated organohydrogensiloxane containing at least one monovalent perfluorooxyalkyl, monovalent perfluoroalkyl, divalent perfluorooxyalkylene or divalent perfluoroalkylene group and at least two hydrosilyl groups in a molecule, and (C) a catalytic amount of a platinum group compound, component (B) being present in an amount to give 0.5 to 5 mol of the hydrosilyl group per mol of the aliphatic unsaturated group in the composition.

3. The compound of formula (1) of claim 1, wherein:

$R^1$ is a monovalent hydrocarbon group of 1 to 10 carbon atoms optionally substituted with halogen atoms, $R^2$ is hydrogen or a monovalent hydrocarbon group of 1 to 10 carbon atoms optionally substituted with halogen atoms, $R^3$ is divalent hydrocarbon group of 1 to 20 carbon atoms optionally substituted by halogen atoms and optionally having at least one intervening —O— group, —NR'— group where R' is hydrogen or alkyl of 1–8 carbon atoms, organosilylene group or a group containing a linear or cyclic organosiloxane, $R^4$ and $R^5$ are, independently, a divalent hydrocarbon group of 1 to 10 carbon atoms optionally substituted with halogen atoms, and a is from 0 to 10.

4. The composition of claim 2, wherein in the formula (1):

$R^1$ is a monovalent hydrocarbon group of 1 to 10 carbon atoms optionally substituted with halogen atoms, $R^2$ is hydrogen or a monovalent hydrocarbon group of 1 to 10 carbon atoms optionally substituted with halogen atoms, $R^3$ is divalent hydrocarbon group of 1 to 20 carbon atoms optionally substituted by halogen atoms and optionally having at least one intervening —O— group, —NR'— group where R' is hydrogen or alkyl of 1–8 carbon atoms, organosilylene group or a group containing a linear or cyclic organosiloxane, $R^4$ and $R^5$ are, independently, a divalent hydrocarbon group of 1 to 10 carbon atoms optionally substituted with halogen atoms, and a is from 0 to 10.

5. The compound of formula (1) of claim 1, wherein Rf is: a divalent perfluoroalkylene group of the formula where m=1–10, or a divalent perfluoropolyether group of one of the following formulae:

wherein X is a F or $CF_3$ group and letters p, q and r are integers in the range $p \geq 1$, $q \geq 1$, and $2 \leq p+q \leq 200$, wherein letters r, s and t are integers in the range: $0 \leq r \leq 6$, $s \geq 0$, $t \geq 0$, and $0 \leq s+t \leq 200$, wherein X is F or $CF_3$ group and letters u and v are integers in the range: $1 \leq u \leq 20$ and $1 \leq v \leq 20$, and wherein w is an integer in the range: $1 \leq w \leq 100$.

6. The composition of claim 2, wherein in formula (1) Rf is: a divalent perfluoroalkylene group of the formula where m=1–10, or a divalent perfluoropolyether group of one of the following formulae:

wherein X is a F or $CF_3$ group and letters p, q and r are integers in the range: $p \geq 1$, $q \geq 1$, and $2 \leq p+q \leq 200$, wherein letters r, s and t are integers in the range: $0 \leq r \leq 6$, $s \geq 0$, $t \geq 0$, and $0 \leq s+t \leq 200$, wherein X is F or $CF_3$ group and letters u and v are integers in the range: $1 \leq u \leq 20$ and $1 \leq v \leq 20$, and wherein w is an integer in the range: $1 \leq w \leq 100$.

7. A compound of claim 1 having a viscosity of about 100 to about 100,000 at 25° C.

8. A composition of claim 2 wherein the compound of formula (1) has a viscosity of about 100 to about 100,000 at 25° C.

9. An elastomer obtained by curing of the composition of claim 2.

10. The composition of claim 2, wherein the fluorinated organohydrogensiloxane, (B), contains at least three hydrosilyl groups in a molecule.

11. The composition of claim 2, wherein the fluorinated organohydrogensiloxane, (B) has at least one perfluorooxyalkyl, perfluoroalkyl, perfluorooxyalkylene or perfluoroalkylene group of one of the following formulae:

wherein m is an integer of 1 to 20, wherein n is an integer of 1 to 5, wherein m+n is an integer of 2 to 100 on average.

12. The composition of claim 2, wherein component (B) is provided in an amount of 0.1 to 50 parts by weight per 100 parts by weight of component (A).

13. The composition of claim 2, further comprising a polysiloxane component containing a $CH_2$=CH(R)SiO unit where R is hydrogen or a substituted or unsubstituted monovalent hydrocarbon group.

14. The composition of claim 2, further comprising an acetylene compound.

15. The composition of claim 2, further comprising an ionic compound of a heavy metal.

* * * * *